United States Patent [19]

Kirsch et al.

[11] Patent Number: 5,527,687
[45] Date of Patent: Jun. 18, 1996

[54] ENZYME INDUCTION SCREEN FOR ERGOSTEROL BIOSYNTHESIS INHIBITORS

[75] Inventors: Donald R. Kirsch, Princeton; Margaret H. K. Lai, East Brunswick, both of N.J.

[73] Assignee: American Cyanamid Company, Wayne, N.J.

[21] Appl. No.: 68,986

[22] Filed: May 25, 1993

[51] Int. Cl.$^6$ .................. C12Q 1/54; C12Q 1/48
[52] U.S. Cl. ............. 435/14; 435/15; 435/7.91; 435/942
[58] Field of Search .................. 435/14, 15, 4, 435/7.9, 7.91, 911, 922, 69.2, 942

[56] References Cited

U.S. PATENT DOCUMENTS 5,236,955  8/1993  Gordon ......................... 514/557

OTHER PUBLICATIONS

Baloch R., Inhibition of Sterol $\rightarrow^8 > \Delta^7$ Isomerase . . . Phytochemistry vol. 26 No. 3 pp. 663–668 1987.
Balliano G., Inhibition of Sterol Biosynthesis . . . Biochim et Biophys Acta 959 1988 pp. 9–19.
Balliano G., Differential Inhibition of Fungal . . . Febs Letters vol. 320 #3 pp. 203–246 1993.
Ausubel, F. M., et al., eds., Current Protocols in Molecular Biology, John Wiley, New York, 1989, Units 13.4, 13.6, 13.7 and 16.4.1.
Basson, M. E., et al., Genetics 117:645–655 (1987).
Casadaban, M. J. et al., Methods Enzymol. 100: 293–308 (1983).
Gaber, R. F., et al., Mol. Cell. Biol. 9: 3447–3456 (1989).
Guarente, L., Methods in Enz. 101: 181–191 (1983).
Hinnebusch, A. G., Micro. Rev. 52: 248–273 (1988).
Ikeura, R., et al., J. Antibiotics 41: 1148–1150.
Kalb, V. F., et al., Gene 45: 237–245 (1986).
Kalb, V. F., et al., DNA 6: 529–537 (1987).
Turi, T. G., and Loper, J. C., J. Biol. Chem. 267: 2046–2056 (1992).

Primary Examiner—William H. Beisner
Assistant Examiner—Ralph Gitomer
Attorney, Agent, or Firm—Darryl L. Webster

[57] ABSTRACT

A method for screening for sterol biosynthesis inhibitors of potential use as fungicides or antihypercholesterolemic agents identifies agents by the induction of lanosterol 14-α-demethylase, an enzyme in the biosynthetic pathway of ergosterol and cholesterol, in cultures containing the agents. In one screening test, test samples are incubated in a culture of a *Saccharomyces cerevisiae* strain sensitive to ergosterol biosynthesis and containing a gene fusion of a lanosterol 14-α-demethylase clone with a gene for bacterial β-galactosidase. After incubation of the culture, an increase in lancsterol 14-α-demethylase activity is determined indirectly by measuring β-galactosidase activity. The culture media contains a chromogenic substrate of β-galactosidase such as orthonitrophenyl-β-D-galactoside or 5-bromo-4-chloro-3-indoyl-β-D-galactoside, so that active samples are identified by the production of colored product. For comparison purposes, screening tests may employ a lanosterol 14-α-demethylase inhibitor such as dinaconazole as a positive control.

18 Claims, No Drawings

ENZYME INDUCTION SCREEN FOR ERGOSTEROL BIOSYNTHESIS INHIBITORS

TECHNICAL FIELD OF THE INVENTION

This invention relates to a screening method for the identification of agents exhibiting potential fungicidal and antihypercholesterolemic activity, based upon the inhibition of ergosterol and/or cholesterol biosynthesis.

BACKGROUND OF THE INVENTION

Ergosterol is the principal membrane sterol of fungi. It is structurally similar to its animal counterpart, cholesterol, except that ergosterol has a methyl group and two double bonds not present in cholesterol. In yeast, ergosterol affects membrane fluidity and permeability and plays an essential role in the yeast cell cycle. Yeast cells can take up cholesterol and decrease their requirement for ergosterol to very low levels, but cholesterol alone cannot completely substitute for ergosterol (Gaber, R. F., et al., *Mol. Cell. Biol.* 9:3447–3456 (1989)).

Though the biosynthesis of ergosterol in fungi involves steps distinct from cholesterol biosynthesis in animals, sterol biosynthesis in different organisms share many common steps. Implicated in sterol biosynthesis is at least one cytochrome P450. The term "cytochrome P450" is a trivial name for a class of cytochromes that includes a number of heme proteins exhibiting a characteristic absorption maximum at 450 nm when combined with CO in the reduced state ('P' denotes pigment; hence, the name). These cytochromes occur in most animal tissues, plants and microorganisms and catalyze the monooxygenation of a vast variety of hydrophobic substances, including lipophilic endogenous compounds and xenobiotics, serving as oxygenating catalysts in the presence of one or more electrontransfer proteins or redox enzymes.

Several distinct cytochrome P450 proteins have been described in yeast and fungi, and the structural genes encoding these proteins, have been isolated (Kalb, V. F., et al., *Gene* 45:237–245 (1986) and Turi, T. G., and Loper, J. C., *J. Biol. Chem.* 267:2046–2056 (1992)). Of these, the most thoroughly characterized is the lanosterol 14-α-demethylase of *Saccharomyces cerevisiae* (ERG11), which was one of the first *S. cerevisiae* enzymes in the ergosterol biosynthetic pathway to be cloned. The sequence of the gene has been published, and the protein shown to be essential for aerobic growth (Kalb, V., et al., *DNA* 6: 529–537 (1987)). This cytochrome P450 catalyzes the oxidative removal of a methyl group at the carbon at position 14 of lanosterol during the biosynthesis of ergosterol; the mammalian orthologue catalyzes the identical reaction in cholesterol biosynthesis. In addition, lanosterol 14-α-demethylase is the specific target of a number of antifungal agents such as ketoconazole, miconazole, econazole, dinaconazole and itraconazole.

Multiple regulatory elements control the expression of the ERG11 gene encoded in *Saccharomyces cerevisiae* (Turi and Loper, cited above). Message levels for the gene increase during yeast growth on glucose, in the presence of heme, during oxygen-limiting conditions, and during anaerobic growth. Genetic analysis indicates there are multiple upstream activating and repressor sequences in the ERG11 promoter (ibid.). At least one of the upstream activating sequences can be activated by other proteins, and repression depends on other repressors. In addition, gene expression appears to be coordinated with the expression of another gene, the CPR1 gene for NADPH-cytochrome P450 reductase, which codes for a flavoprotein that serves as an electron transfer enzyme from NADPH to cytochrome P450 and thus acts in concert with it (ibid.). Complicating this complex regulation system are the mechanisms controlling overall gene regulation in yeast (reviewed by Hinnebusch, A. G., *Micro. Rev.* 52:248–273 (1988)).

SUMMARY OF THE INVENTION

It is an object of the invention to provide a screening test for the identification of potential fungicides for a wide variety of agricultural, medical, and veterinary products and potential antihypercholesterolemic agents for medical and food products.

It is a further and more specific object of the invention to identify potential agents that inhibit ergosterol and cholesterol biosynthesis.

These and other objects are accomplished by the present invention, that provides a method for the identification of agents which inhibit ergosterol or cholesterol biosynthesis and thus induce lanosterol 14-α-demethylase activity in response to cellular starvation for sterol caused by the action of the agent. The method is a screening test whereby test samples are incubated in a yeast culture, and lanosterol 14-α-demethylase activity is measured. Increased activity indicates enzyme induction and sterol biosynthesis inhibition.

In the practice of this invention's method for screening for the presence or absence of sterol biosynthesis inhibition reflected as induced lanosterol 14-α-demethylase activity by a test sample, the test sample is added to a culture or culture area of *Saccharomyces cerevisiae*. Preferred embodiments employ a *S. cerevisiae* strain sensitive to ergosterol biosynthesis. The cultures are incubated with the test sample for such time under such conditions sufficient to observe yeast cell growth, ordinarily monitored in a corresponding culture or culture area containing no test sample. Enhanced lanosterol 14-α-demethylase activity is assessed, generally by comparing the extent of enzyme induction in the culture or culture area containing the test sample with the extent of enzyme induction in the culture or culture area containing no test sample. In especially preferred embodiments, a known inhibitor of lanosterol 14-α-demethylase such as dinaconazole or ketoconazole is used as a positive control and incubated with the test sample to assist in the identification of active agents.

Enzyme induction is measured by measuring an increase in enzyme activity directly or indirectly. Direct measurements are made using conventional assays for lanosterol 14-α-demethylase, which include spectral analyses, tracer studies, and antibody reactions involving enzyme substrates and/or products and the like, but simpler indirect measurements are preferred. In indirect measurements, the enzyme is tagged with an easily identified marker, and induction is observed by measuring an increase in the marker. In yeast, the enzyme β-galactosidase is typically employed as a marker because it hydrolyzes a variety of β-galactosides including chromogenic substrates that yield colored, easily visually or spectroscopically perceptible products when hydrolyzed. Potentially active agents are identified by the observation of the β-galactosidase colored product.

In a particularly preferred embodiment, the coding sequence for yeast lanosterol 14-α-demethylase is fused with the structural gene for *Escherichia coli* β-galactosidase and this fusion is inserted into a *S. cerevisiae* strain sensitive to ergosterol biosynthesis such as a strain lacking isozyme 1 of hydroxymethylglutaryl CoA (HMGCoA) reductase of the sterol synthetic pathway, hmg1⁻. This strain exhibits compromised ergosterol biosynthesis. Alternatively, other mutants exhibiting partial function loss are useful. An example of such a *S. cerevisiae* strain is JRY1159(pML74) described in the Examples. The strain is grown in a solidified media containing a chromogenic β-galactosidase substrate such as orthonitrophenyl-β -D-galactoside (ONPG) or 5-bromo-4-chloro-3-indoyl-β-D-galactoside (X-Gal) in a plate or dish, so that test samples and positive controls on disks or wells can be observed visually and simultaneously as regions of the same culture. Actives produce a halo of color around test samples grown in a lawn of the culture. Using ONPG, the halo is yellow and using X-Gal, it is blue.

DETAILED DESCRIPTION OF THE INVENTION

The screening method of this invention is based upon the finding that a Saccharomyces cerevisiae strain containing a cloned gene encoding lanostrol 14-α-demethylase fused to a gene for β-galactosidase and exhibiting sensitivity to ergosterol biosynthesis is useful for a rapid and sensitive screening assay for large numbers of potential inhibitors of ergosterol biosynthesis. Test samples which inhibit ergosterol biosynthesis in this system induce lanosterol 14-α-demethylase activity in the culture, and, because of the gene fusion in the strain, an easily measured increase in β-galactosidase activity is observed in cultures containing a chromogenic β-galactosidase substrate.

In the practice of this invention, a chemical or biochemical test sample is added to a culture or culture area of baker's yeast, *Saccharomyces cerevisiae*, and indication of sterol biosynthesis inhibition is made by observing induced lanosterol 14-α-demethylase activity caused by yeast response to depletion of ergosterol, which stimulates synthesis of the enzyme.

Preferred embodiments employ a *S. cerevisiae* strain sensitive to ergosterol biosynthesis so that induction is more pronounced where it occurs, and side effects that potential agents have on yeast metabolism are minimized. Any strain sensitive to ergosterol biosynthesis may be employed, such as viable strains exhibiting diminished or compromised ergosterol biosynthesis. A typical strain is one carrying a hmg1⁻ mutation that lacks the major isozyme for hydroxymethylglutaryl CoA (HMGCoA) reductase (HMG1), an enzyme catalyzing the first committed step to ergosterol biosynthesis. Cells lacking this isozyme are viable because another isozyme (HMG2) provides about 15% of the enzyme activity observed in wild-type strains, but the mutant is significantly compromised for sterol biosynthesis. Other useful strains include those exhibiting partial function loss such as erg8 mutants and the like.

Enzyme induction of 14-α-demethylase is measured by measuring an increase in enzyme activity in the culture. Direct measurements are made using conventional assays for lanosterol 14-α-demethylase, which include spectral analyses of the cytochrome heme group, tracer studies of oxygen uptake or demethylation, and antibody reactions to the enzyme substrates and/or products. These tests are tedious and require special reagents and equipment.

Simpler indirect measurements of enzyme activity are preferred. In indirect measurements, the enzyme is tagged with an easily identified marker, and induction is observed by measuring an increase in the marker. Any type of marker is useful, including radioactive labels, genetic tracers including enzyme tags, and antibodies reactive to particular antigens involved in the enzymatic reaction or to other tags. Enzyme tags are especially preferred for the practice of this invention because many can be located using chromogenic substrates or products, thereby making measurement by observing color change or development simple, easy, and less expensive than those involving radioactivity or antibody production.

Since the gene for 14-α-demethylase has been cloned, tags to it, especially enzyme tags, are readily introduced into yeast cultures using gene fusion following standard procedures (summarized in Guarente, L., *Methods in Enz.* 101:181–191 (1983) and Ausubel, F. M., et al., eds., *Current Protocols in Molecular Biology,* John Wiley, New York, 1989, Units 13.4, 13.6, 13.7 and 16.4.1). The clone is introduced into a vector having a carrier sequence or tracer coding for a protein that can be easily located using enzyme assays, affinity purification techniques or readily available antibodies, such as β-galactosidase, glutathione-S-transferase, and the like. Many of the tracers commonly employed for this purpose are bacterial proteins, notably those from *Escherichia coli,* and plasmids containing them, such as those in the YIp, YRp, YCp and YEp classes, which are conveniently maintained both in *E. coli* and *S. cerevisiae*. After fusion, the fused gene product coding for the tagged enzyme is introduced into yeast using standard transformation techniques using plasmids or any other means including lithium acetate, spheroplasts, or electroporation transformation.

In yeast, the enzyme β-galactosidase is typically employed as a marker because it readily hydrolyzes a variety of β-galactosides including chromogenic substrates which yield a colored, easily visually or spectroscopically perceptible product when hydrolyzed. For rapid assays, the β-galactosidase substrate is grown in the yeast culture, and the assays are sensitive. β-Galactosidase substrates include, but are not limited to, orthonitrophenyl-β -D-galactoside (ONPG), 5-bromo-4-chloro-3-indoyl-β-D-galactoside (X-Gal), phenyl-β-D-galactoside (P-Gal), paranitrophenyl-β-galactoside, and 6-O-β-D-galactopyranosyl-D-glucose (allolactose). Preferred substrates for introduction into the yeast cultures are ones which do not inhibit cell growth, do not depend on other gene products for activity and do not induce other operons. The chromogenic substrates X-Gal and ONGP are especially preferred, yielding blue and yellow chromogens, respectively. X-Gal is preferred for solidified cultures and ONPG for liquid cultures.

The well studied lacZ gene of *Escherichia coli* encodes the β-galactosidase enzyme, and therefore lacZ fusions to yeast genes are commonly employed in yeast genetics as markers (Ausubel, cited above, Unit 13.6 and Guarente, L., *Methods in Enz.* 101:181–191 (1983)). Yeast clone fusions are constructed such that the promoter region of the yeast gene—plus several amino acids from the N terminus of the protein encoded by this gene—is fused to the carboxy-terminal region of the lacZ gene, which encodes a protein fragment that still retains galactosidase activity.

In a particularly preferred embodiment, the coding sequence for lanosterol 14-α-demethylase is fused with the structural gene for *Escherichia coli* β-galactosidase, and this fusion is inserted into the *S. cerevisiae* strain sensitive to ergosterol biosynthesis previously described. Since the gene for lanosterol 14-α-demethylase in *S. cerevisiae* has been cloned, this clone is fused to the lacZ gene of *E. coli* using standard procedures as set out in Ausubel, et al., or Guarente, previously cited. Typically, these involve the construction of a fusion of lacZ and a yeast sequence containing a marker such as URA3 in a lacZ plasmid vector which can be readily transformed into yeast such as pLG670-Z, pLG200 or pLG400.

Fusions of the lanosterol 14-α-demethylase gene to lacZ in plasmid vectors and insertion of these into yeast have been described by Turi and Loper, cited hereinabove. One fusion, for example, was carried out by these investigators by first removing the entire ERG11 coding region except for the translation initiation ATG codon by digesting plasmid PVK11 with BclI followed by treating with Bal31 exonuclease. Termini of the partially deleted plasmids were filled in with DNA polymerase I, ligated with HindIII linkers, digested with HindIII, and religated in dilute solution to form circular plasmids. A plasmid (pTT70) was identified that had a HindIII linker adjacent to the ATG codon. This region when ligated to the promoterless lacZ gene of plasmid YEp352 produced an in-frame ERG11-lacZ fusion, which was inserted into a number of yeast strains.

Simpler procedures involve the transformation of yeast strains with plasmids containing the lanosterol 14-α-demethylase and lacZ fusion. In one embodiment of this invention, about 2.5 kilobases of promoter and upstream sequences and the initial 102 base pairs of coding sequence from a lanosterol 14-α-demethylase clone are fused with the structural gene for the bacterial enzyme, β-galactosidase from *E. coli* by ligating plasmid DNA encoding the genes, and transforming a yeast hmg1⁻ mutant denoted JRY1159 with a plasmid containing the fusion denoted pML74, resulting in a yeast strain denoted JRY115-9(pML74). Details of the experimental protocol are given in Example 1 below.

In the preferred practice of this invention's method, a test sample is added to a culture or culture area of a Saccharomyces cerevisiae strain exhibiting diminished or compromised ergosterol biosynthesis and containing the gene fusion coding for lanosterol 14-α-demethylase and β-galactosidase. The culture media contains a chromogenic β-galactosidase substrate such as orthonitrophenyl-β-D-galactoside (ONPG) or 5-bromo-4-chloro-3-indoyl-β-D-galactoside (X-Gal). The cultures are incubated with the test sample for such time under such conditions sufficient to observe yeast cell growth in corresponding cultures or culture areas of the yeast strain containing no test sample. The presence of induction of lanosterol 14-α-demethylase is determined by observation of color changes in the media caused by β-galactosidase action on its substrate. Using ONPG, the color is yellow and using X-Gal, it is blue. X-Gal is especially preferred.

In especially preferred embodiments, a known inhibitor of lanosterol 14-α-demethylase such as dinaconazole, ketoconazole, miconazole, econazole, or itraconazole is used as a positive control and incubated with the test sample to assist in the identification of potential agents. Diniconazole is employed in one embodiment; as little as ~25 ng is detected using the method of this invention. The positive control is employed both as a test of whether a particular culture is functioning properly and as a standard for color development.

Any type of solidified or liquid media that will support growth and reproduction of the *S. cerevisiae* strain is useful in cultures for practicing the method of this invention. Numerous yeast media are known to the skilled artisan, and an advantage of the invention is that baker's yeast is relatively easy to grow. Typical media are yeast extract, peptone and dextrose (YEPD) or yeast extract and dextrose (YED) media; yeast basal growth media (YBGM) containing glucose, vitamins, minerals, and water; yeast, peptone, and adenine sulfate (YPA) media; yeast mannitol (YM) media and YM plus glucose; synthetic dextrose (SD) media containing dextrose, a yeast nitrogen base, and water and optionally containing amino acids, adenine sulfate and uracil; and the like. Preferred media are solidified by adding agar or gelatin; especially preferred are agar solidified media.

Where liquid cultures are employed, differences in color development in cultures grown with no sample are compared to those grown with test samples and controls. Color development is generally measured spectrophotometrically, corrected for light scattering by cell debris and absorbance by other reagents. Where ONPG is the chromogen, yellow color is typically measured at 400 to 430 nm. Where X-Gal is the chromogen, blue color is typically measured at 600 to 640 nm.

In the practice of preferred embodiments of this invention, however, solidified media in a plate or dish is preferred. In this way, test samples and positive controls on disks or wells are observed simultaneously as regions of the same culture and positives identified immediately by visual inspection. Blue is easier to see and, as such, X-Gal is preferred for plated cultures. Actives produce a halo of color around test samples grown in a lawn of the culture. The halo surrounds a zone of growth inhibition.

An advantage of the invention is its speed and simplicity. A large number of samples are tested quickly and inexpensively. Inhibitors of multiple enzymes in the ergosterol biosynthetic pathway are detected in a single screen that is useful for screening synthetic compounds or natural products such as fermentation broths or plant extracts. Because of the close similarity of sterol biosynthetic pathways, actives in the screening method are not only potential fungicides but also potential antihypercholesterolemic agents.

It is another advantage of this invention that it is sensitive, and only small amounts of biochemical or chemical agents are required for the test. In a standard assay, for example, which employs solidified media in a plate, as little as 20 µg of a biochemical or chemical For fermentation broths, however, higher concentration may be necessary and concentrations as high as 200-fold or higher are employed.

The method of this invention assay has a moderate positive rate (>0.02%), so that secondary tests may be considered to prioritize actives found using the screen. Standard in vitro and in vivo fungicide discovery screens can be employed for this. In vitro screens test samples for their ability to inhibit the growth of selected phytopathogenic fungi cultured in nutrient agar. These include fungi causing wheat eyespot (*Pseudocercosporella herpotrichoides*), rice sheath blight (*Rhizoctonia solani*) and damping off (*Fusarium oxysporum*), which all synthesize ergosterol. In in vivo screens, a variety of phytopathogenic fungi are used to infect plants treated with test compounds. Active compounds block or reduce the appearance of disease symptoms. A number of model plant infections can be employed in the screen and include ergosterol-producing fungi causing apple scab (*Venturia inaequalis*), pepper botrytis (*Botrytis cincerea*), rice blast (*Pyricularia oryzae*), sugar beet cercospora (*Cercospora beticola*), tomato early blight (*Alternaria solani*), wheat leaf rust (*Puccinia recondita tritici*), and wheat powdery mildew (*Erysiphe graminis tritici*).

The following examples are presented to further illustrate and explain the present invention and should not be taken as limiting in any regard.

EXAMPLE 1

This example illustrates the preparation of JRY1159 (pML74), a hmg1⁻ yeast mutant having a gene fusion of yeast lanosterol 14-α-demethylase to bacterial β-galactosidase that is useful in the assays of Example 2 below.

Briefly stated, a plasmid containing about 2.5 kilobases of promoter and upstream sequences and the initial 102 base pairs of the coding sequence of lanosterol 14-α-demethylase is fused to an *E. coli* lacZ DNA sequence by cleaving the plasmid, converting cohesive ends obtained in the cleavage to flush ends, inserting the lacZ sequence by ligation, and testing the plasmid so obtained by transformation into a URA3 yeast strain prior to transformation into the hmg1⁻ strain.

Plasmid pVK11 is prepared as described by Kalb, 1986. Haploid yeast strain JL10 (BWG 2-9A, genotype MATα, adel- 100, his4-419, ura3-52) is transformed with a library constructed from a haploid strain congenic to strain S288C by insertion of DNA fragments obtained by partial Sau3A digestion, into the BamHI site of URA3-containing plasmid YEp24. The top agar containing about 31,000 Ura⁺ colonies is homogenized and stored at −20° C. An aliquot ($10^5$ cells) of the homogenate is subcultured for 8 hours in 2 ml SD medium containing 2 µg Kc (ketoconazole)/ml. Using this subculture, 15 plates of SD-agar medium containing 4 µg Kc/ml are inoculated with 400 cells/plate. About four colonies per plate are obtained. The 15 largest colonies are suspended separately in saline and 30 colony-forming units from each suspension are inoculated into YPD medium containing 8 µg Kc/ml.

Incubation for three days at 30° C. in a roller drum yields growth in seven of the 15 tubes. A clone is isolated from each of these seven. Two of these clones are selected for further study based upon results from tests of concomitant loss of uracil independence and Kc resistance. DNA from each of the two strains is used to transform *E. coli* to ampicillin resistance. Each of these transformant populations serve as the source of an individual plasmid clone. These two plasmids, designated pVK1 and pVK2, contain genomic inserts of 9.3 and 8.2 kb, respectively. The plamids confer Kc resistance and 3 to 6 times the cellular levels of P-450 to both yeast strains JL10 and JL745 (MATα, his, ade, trp, ura3-52, derived from a cross between JL10 and a haploid isolate from D5). Hybrid selection and in vitro translation show both plasmids contain structural gene sequences for cytochrome P 450 proteins that cross react with antibody preparations. Restriction mapping show that pVK1 and pVK2 overlap, and subclone pVK11 produced from pVK1 (pUC8+4.7 kb HindIII-BamHI subfragment of pVK1) contains this overlapping region.

Twenty µg plasmid pVK11 encoding lanosterol 14-α-demethylase in 16 µl water is digested with 20 µl BclI (from BRL, 100 units) in 40 µl 10×React 2 buffer from BRL and 324 µl water at 60° C. for 2 hours (BRL is Gibco BRL Life Technologies, Gaithersberg, Md.). The reaction is stopped by adding 12 µl 5 M NaCl, and extracted with 400 µl chloroform:isoamyl alcohol (IAA, 24:1). To the aqueous phase, 100 µl 95% ethanol are added to precipitate the DNA, and the DNA is dissolved in 20 µl water. The protruding 3'-end is removed by diluting 15 µl in 132 µl 2×T4 polymerase buffer and 108 µl water, adding 9 µl T4 polymerase (3 units, obtained from BRL), and incubating the mixture for 45 minutes at 30° C. The reaction is stopped by adding 10.6 µl 5 M NaCl, 275 µl chloroform:IAA (24:1). The DNA is precipitated by adding 687 µl 95% ethanol, dissolved in 20 µl 10×React 3 buffer from BRL, 12 µl EcoR1 (120 units, from BRL), and 168 µl water, held at 37° C. for 18 hours, and run on 0.8% agarose gel. The 2.5 kb middle band is cut out, and the DNA is purified from the gel using GENECLEAN® purchased from BIO101(BI0101 is Bi0101 Inc., LaJolla, Calif.).

Six µg plasmid pMC2010 containing the lacZ sequence (Casadaban, M. J. et al., *Methods Enzymol.* 100:293–308 (1983)) in 20 µl water is digested with 6 µl SmaI (600 units, from BRL) in 12 µl 10×React 4 buffer from BRL and 88 µl water for 1 hour at 37° C. The reaction is stopped by adding 3.6 µl 5M NaCl and 125 µl chloroform:IAA (24:1), and DNA is precipitated by adding 312 µl 95% ethanol and is dissolved in 20 µl water.

The purified DNA with sticky EcoR1 ends and blunt-ended BclI ends, coding lanosterol 14-α-demethylase, 0.6 µg, is ligated with 0.25 µg of the EcoR1, SmaI-cleaved pMC2010 by incubating with 1 µl T4 ligase (2 units, from BRL) in 45 µl 1×T4-ligase buffer, and 22.5 µl is transformed into 100 µl *E. coli* strain JM101 (from BRL, having genotype supE, thi-1, Δ(lac-proAB), [F'traD36, proAB, lacZΔM15]) and plated on agar containing X-Gal (80 µg/ml) and ampicillin (50 µg/ml). Blue colonies obtained are streaked on LB containing X-Gal and ampicillin to obtain single cultures, and 1 ml overnight culures grown in LB broth containing ampicillin to prepare mini DNA preparations to cut with ClaI and BamH1 and check the construction of the fusion. A plasmid showing the appropriate construct is transformed into trp1⁻ yeast strains and tested with a ketoconazole positive control on YBGM culture plates containing vitamins, amino acids and X-Gal.

A 2.5 kb BamH1 fragment of the plasmid containing the fusion is then inserted into the BamH1 site of pMC1585 (lacZ, URA3). Five µg of the plasmid containing the fused gene and 10 µg pMC1585 are incubated separately with 3 µl BamH1 (30 units, from BRL) in 100 µl 10×React 3 buffer from BRL. The DNA with the fused gene is run on acrylamide gel, the lower bands (2 kb) cut, and the purified material is dissolved in 15 µl water. This is extracted with GENECLEAN®. Plasmid pML1585 cut with BamHI is precipitated with ethanol. The fragments are ligated with T4 ligase (1 µl, 2 units, from BRL) in 20 µl 5×ligase buffer and 76 µl water. The ligation mix is transformed into *E. coli* strain JM101, and plated on LB agar plate containing X-gal and ampicillin, and blue colonies are streaked on the same media. The DNA isolated from blue colonies are cut with BamHI, ClaI, EcoR1, and BglII to verify that the DNA is the correct construct.

The plasmid, denoted pML74, is then transformed into JRY1159, a ura3, hmg1⁻ mutant to URA3⁺ (genotype MATa hmg1::LYS2, HMG2, ura3-52, his3Δ200, lys2-801, ade2-101, met, Basson, M. E., et al., *Genetics* 117:645–655 (1987)). An overnight culture grown in SD media is inoculated in YBGM supplemented with casamino acids, adenine, vitamins, and X-Gal, and tested in cultures grown for 4 days with the Table I fungicide panel representing varied mechanisms of action.

TABLE I

| STANDARD FUNGICIDE PANEL | |
|---|---|
| Compound | Target |
| amphotericin B | plasma membrane (polyene) |
| cerulenin | fatty acid biosynthesis |
| haloprogin | respiration |
| ketoconazole | ergosterol biosynthesis |

TABLE I-continued
STANDARD FUNGICIDE PANEL

| Compound | Target |
|---|---|
| miconazole | (lanosterol 14α-demethylase) ergosterol biosynthesis |
| dinaconazole | (lanosterol 14α-demethylase) ergosterol biosynthesis |
| econazole | (lanosterol 14α-demethylase) ergosterol biosynthesis |
| fenarimole | (lanosterol 14α-demethylase) ergosterol biosynthesis |
| tridemorph | (sterol Δ14 reductase) ergosterol biosynthesis |
| tolnaftate | (sterol Δ14 reductase) ergosterol biosynthesis (squalene monooxygenase) |
| U18666A | ergosterol biosynthesis (squalene cyclase) |
| cycloheximide | protein biosynthesis |
| polyoxin D | chitin biosynthesis (cell wall) |
| nikkomycin | chitin biosynthesis (cell wall) |
| nocodazole | microtubule |
| benomyl | microtubule |
| maneb | multi-target |
| metalaxyl | rRNA biosynthesis |
| vinclozolin | lipid peroxidation |
| kanamycin | mitochondria |
| tunicamycin | glycoprotein biosynthesis |
| carboxin | succinate dehydrogenase |
| cyanobutarate | microtubule (plant) |
| antimycin | respiration |
| 5-fluoro-cytosine | nucleotide metabolism |
| glyphosate | herbicide (aromatic amino acid biosynthesis) |
| phosphinothricin | herbicide (glutamine biosynthesis) |
| aminotriazole | herbicide (histidine biosynthesis) |
| sulfometuron methyl | herbicide (branched chain amio acid biosynthesis) |
| pendimethalin | herbicide (microtubule) |

Only known inhibitors of sterol biosynthesis, ketoconazole, miconazole, dinaconazole, econazole, fenarimole and tridemorph are active with the yeast strain.

EXAMPLE 2

This example illustrates the method of this invention and its use in the screening of numerous biochemical and chemical test samples for activity in inhibiting ergosterol biosynthesis.

Components of the test media are first prepared using analytical grade or cell culture tested reagents obtained from the sources indicated in parenthesis.

A mineral salts solution is prepared by mixing

| | |
|---|---|
| $MgSO_4$ (Baker) | 19.6 gm |
| $FeCl_3.6H_2O$ (Baker) | 0.1 gm |
| Distilled Water | 200 ml |

The solution is stored in non-sterile conditions at room temperature.

Yeast basal growth media, YBGM, part A, is prepared by mixing:

| | |
|---|---|
| Glucose (Difco or Sigma) | 40 gm |
| Agar (Difco) | 40 gm |
| Distilled Water | 1000 ml | and autoclaving at 20 lbs for 15 min. YBGM, part B, is prepared by mixing

| | |
|---|---|
| $KH_2PO_4$ (Mallinckrodt) | 27.2 gm |
| KOH (Mallinckrodt) | 8.4 gm |
| $(NH_4)_2SO_4$ (Sigma) | 4 gm |
| Mineral Salts Solution | 2 ml |
| Distilled Water | 1000 ml | and autoclaving at 20 lbs for 15 min. Components A and B are combined after sterilization and are then stored.

A vitamin stock solution is prepared by mixing

| | |
|---|---|
| Pantothenic Acid (Sigma) | 4 mg |
| Pyridoxine.HCl (Sigma) | 4 mg |
| Myo-inositol (Sigma) | 20 mg |
| Biotin (Sigma, 100 µg/ml stock) | 2.5 ml |
| Thiamine·HCl (Sigma) | 4 mg |
| Distilled Water | 100 ml | and filter sterilizing. The solution is stored at −20° C. in 3 ml aliquots.

A nutrient solution is prepared by mixing

| | |
|---|---|
| Casamino Acids (Difco) | 25 gm |
| Adenine Sulfate | 200 mg |
| Distilled Water | 100 ml | and filter sterilizing. The solution is stored at room temperature protected from the light.

An X-gal (5-bromo-4-chloro-3-indoyl-β-D-galactoside) stock solution is prepared by mixing

| | |
|---|---|
| X-gal (NJ Lab Supply) | 40 mg |
| DMSO (Baker) | 1 ml |

The solution is stored at −20° F. protected from the light.

A minimal synthetic dextrose (SD) media containing salts, trace elements, vitamins, a nitrogen source and dextrose is prepared by combining

| | |
|---|---|
| Yeast Nitrogen Base (without amino acids, Difco) | 7 gm |
| Dextrose (Sigma) | 20 gm |
| Distilled water | 1000 ml | and autoclaving at 20 lbs for 15 min. One colony of strain JRY1159(pML74) described in Example 1 above is inoculated into 50 ml of this liquid media supplemented with 1/100 volume nutrient solution and shaken at 30° C. The culture is grown to an $OD_{600}$ of ~2.5 or greater, while being shaken at 30° C. This is used as the culture inoculum for testing.

Test media is prepared by combining

| | |
|---|---|
| YBGM Media | 1 volume |
| Vitamin Stock Solution | 1/100 volume |
| Nutrient Stock Solution | 1/100 volume |
| X-Gal Stock | 1/1000 volume |
| JRY1159(pML74) Culture Inoculum | 1/100 volume |

The assay protocol is summarized as follows. Pour plates and place test samples on plates. A ¼" disk containing 10 µg of dinaconazole is used as a positive control. This gives a clear positive response. Alternatively, disks with several concentrations around the detection limit for dinaconazole (~25 ng) are useful to demonstrate the level of sensitivity in a given assay. The plates are incubated at 30° C. for two days and then examined for activity. Actives produce blue halo (that may surround a zone of growth inhibition) around the test sample.

Table I above presents a panel of standard fungicides tested using this method, including both natural and synthetic compounds chosen to represent a wide variety of mechanisms of action. At a level of 20 μg/disk, none of the compounds are active in the ergosterol biosynthesis induction screen described with the exception of known ergosterol biosynthesis inhibitors, ketoconazole, miconazole, dinaconazole, econazole, fenarimole and tridemorph.

Table II lists a panel containing 70 varied antibiotic types.

TABLE II

STANDARD ANTIBIOTIC PANEL

| | |
|---|---|
| pimaricin (tennecetin) | streptogramin ("type") |
| monazomycin | nystatin |
| aspartocin | bacitracin |
| clavacin | citrinin |
| avoparcin | isoguinocycline |
| neutramycin | A1531 |
| leucomycin | A0341β |
| angustmycin A & C | gliotoxin |
| gibberellic acid | puromycin |
| puromycin aminonucleoside | BM123α |
| etamycin | mocimycin |
| neomycin | viomycin |
| netropsin | lincomycin |
| picromycin | A9537 |
| AN272α | levomycin |
| AM374 | antiprozoin |
| BL580 zeta | actithiazic acid |
| hamycin | carbomycin |
| frenolicin | fusarinic acid |
| BL580α | tylosin |
| declomycin | tetrahydro spiramycin |
| usnic acid | geldanamycin |
| Z122OA | BM782ε |
| BO2964 complex | choramphenicol |
| A8363 | actinomycin |
| BM123γ | AD97 |
| phenazine α | paromomycin |
| streptomycin | A4825 |
| alazopeptin | nucleocidin |
| nonactin | valinomycin |
| C19004 complex | avilamycin |
| V214W | V214X |
| vancomycin | ristocetin |
| relomycin | CO8078α |
| blasticidin S | 4-dedimethylamino-4-methyl-amino-anhydrotetracycline |

When tested at a level of 20 μg/disk in the same assay, four of the compounds are active. They are antiprozoin, geldamycin, BM123$_\gamma$, and tennectetin. Literature reports on these compounds indicate they are not inhibitors of sterol biosynthesis, although there are suggestions that they might all have direct actions on the fungal membrane.

A subsequent screen of about 7000 compounds yields only 7 actives (~0.1%). It is highly unlikely that all of these compounds are primarily ergosterol biosynthesis inhibitors. Therefore, while the screen is selective and identifies a large variety of ergosterol biosynthesis inhibitors, compounds with other mechanisms of action are identified as well.

The assay is used to screen over 17,000 fermentation samples, and actives are observed at a rate of ~0.13%. Of these active test samples, two are tested in other fungicide discovery screens and neither are active. Experiments to determine the nature of the active component in these samples indicate the presence of polyether antibiotics which may be responsible for the positive result in the assay of this invention. Two other active test samples contain polyene antibiotics. A third active test sample contains a lipopeptide antibiotic.

The assay is further tested using compactin, a specific potent inhibitor of 3-hydroxy-3-methylglutaryl (HMG)-CoA reductase, the major rate-limiting enzyme in the biosynthesis of isoprenoid compounds (Ikeura, R., et al., *J. Antibiotics* 41:1148–1150 (1988)). In the assay of this invention, lactonized mevinolin (monacolin K, obtained from Merck) produces a weak response when used at high levels (20 μg).

EXAMPLE 3

For comparative purposes, the assay of Example 2 is carried out using other yeast strains containing the lanosterol 14-α-demethylase fusion to β-galactosidase besides the hmg1⁻ mutant of Example 1.

When the fusion is inserted into a wild-type yeast (M12B, MATα genotype ura3, trp1) screens of the panel of fungicides listed in Table I produce a clear induction response with all ergosterol biosynthesis inhibitors. However, a number of fungicides with other modes of action including amphotericin B, cerulenin, cycloheximide, 5-F-cytosine, and amino-triazole also produce an induction response, suggesting that induction is not a specific indicator of sterol biosynthesis inhibition. One explanation for this lack of specificity is the presence of sequences resembling TGACTC in the upstream region of lanosterol 14-α-demethylase, which are known to respond to the GCN4 protein, a transcriptional regulator in yeast which mediates a wide variety of responses (Hinnebusch, A. G., cited above). To test this hypothesis, induction is virtually abolished when the fusion construction is introduced into a gcn4⁻ mutant host.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are meant to cover the claimed components and steps in any sequence which is effective to meet the objectives there intended, unless the context specifically indicates the contrary.

BIBLIOGRAPHY

Ausubel, F. M., et al., eds., *Current Protocols in Molecular Biology*, John Wiley, New York, 1989, Units 13.4, 13.6, 13.7 and 16.4.1.
Basson, M. E., et al., *Genetics* 117:645–655 (1987).
Casadaban, M. J. et al., *Methods Enzymol.* 100:293–308 (19S3).
Gaber, R. F., et al., *Mol. Cell. Biol.* 9:3447–3456 (1989).
Guarente, L., *Methods in Enz.* 101:181–191 (1983).
Hinnebusch, A. G., *Micro. Rev.* 52:248–273 (1988).
Ikeura, R., et al., *J. Antibiotics* 41:1148–1150 (1988).
Kalb, V. F., et al., *Gene* 45:237–245 (1986).
Kalb, V. F., et al., *DNA* 6: 529–537 (1987).
Turi, T. G., and Loper, J. C., *J. Biol. Chem.* 267:2046–2056 (1992).

We claim:

1. A method for screening for the presence or absence of inhibition of ergosterol biosynthesis by a test sample, said method comprising:

(a) adding said test sample to a culture of *Saccharomyces cerevisiae;* wherein said culture of *Saccharomyces cerevisiae* comprises a strain containing a clone of lanosterol 14-α-demethylase gens fused to a gens encoding β-galactosidase and said strain is sensitive to ergosterol biosynthesis (b) incubating said test sample in said culture for such time under such conditions sufficient to observe yeast cell growth in a corresponding culture containing no test sample;

(c) assaying for activity of lanosterol 14-α-demethylase in both the culture containing the test sample and the corresponding culture containing no test sample; and (d) determining the presence of ergosterol biosynthesis inhibition by observation of whether the level of activity of the lanosterol 14-α-demethylase in the culture containing the test sample exceeds the level of activity in the corresponding culture containing no test sample.

2. A method according to claim 1 wherein said strain contains a hmg1⁻ mutation.

3. A method according to claim 2 wherein said strain is JRY1159 (pML74).

4. A method according to claim 1 wherein the level of activity of lanosterol 14-α-demethylase is determined by an assay for β-galactosidase activity.

5. A method according to claims 4 wherein said assay for β-galactosidase activity employs a substrate selected from the group consisting of orthonitrophenyl-β-D-galactoside, 5-bromo-4-chloro-3-indoyl-β-D-galactoside, phenyl-β-D-galactoside, paranitrophenyl-β-galactoside, and allolactose.

6. A method according to claim 5 wherein said substrate is selected from the group consisting of orthonitrophenyl-β-D-galactoside and 5-bromo-4-chloro-3-indoyl-β-D-galactoside.

7. A method according to claim 1 wherein said culture and said corresponding culture comprise one solidified culture and test samples are added to areas of the cultures on a disk or in a well.

8. A method according to claim 7 wherein a positive control comprising a lanosterol 14-α-demethylase inhibitor is applied to another disk or a well on the culture.

9. A method according to claim 8 wherein said inhibitor is selected from the group consisting of ketoconazole, miconazole, econazole, dinaconazole, and itraconazole.

10. A method for screening for the presence or absence of inhibition of ergosterol biosynthesis by a biochemical or chemical test sample, said method comprising:

(a) adding said test sample to a culture of a *Saccharomyces cerevisiae* strain sensitive to ergosterol biosynthesis and containing a gene fusion of a yeast lanosterol 14-α-demethylase clone with a structural gene for bacterial β-galactosidase;

(b) adding to a corresponding culture a positive control comprising a known lanosterol 14-α-demethylase inhibitor;

(c) incubating the test sample culture and the positive control culture for such time under such conditions sufficient to observe yeast cell growth in the positive control;

(d) assaying for beta-galactosidase activity in the test sample culture and the positive control culture of step (c); and (e) determining the presence or absence of inhibition of ergosterol biosynthesis of the test sample by correlating the level of activity of beta-galactosidase in the positive control culture to the level of activity of beta-galactosidase in the test sample culture, wherein if the level of activity of beta-galactosidase in the positive control culture exceeds that of the test sample culture, the presence of inhibition of ergosterol biosynthesis is indicated.

11. A method according to claim 10 wherein the *Saccharomyces cerevisiae* strain sensitive to ergosterol biosynthesis contains a hmg1⁻ mutation.

12. A method according to claim 11 wherein the gene fusion of a yeast lanosterol 14-α-demethylase clone with a structural gene for bacterial β-galactosidase comprises a *E. coli* lacZ fusion with a lanosterol 14-α-demethylase clone containing upstream promoter sequences and sequences for structural lanosterol 14-α-demethylase.

13. A method according to claim 12 wherein β-galactosidase activity is assayed using a substrate selected from the group consisting of orthonitrophenyl-β-D-galactoside and 5-bromo-4-chloro-3-indoyl-β-D-galactoside.

14. A method according to claim 13 wherein said Saccharomyces cerevisiae is cultured in solidified media containing the β-galactosidase substrate, the test sample and positive control are applied to a disk or a well in the same culture, and an active sample is identified by a halo of color around the disk or well after incubation of the culture.

15. A method according to claim 14 wherein said positive control is selected from the group consisting of ketoconazole, miconazole, econazole, dinaconazole, and itraconazole.

16. A method according to claim 14 wherein the β-galactosidase substrate is 5-bromo-4-chloro-3-indoyl-β-D-galactoside and the halo of color is blue.

17. A method for screening for the presence or absence of inhibition of ergosterol biosynthesis by a biochemical or chemical test sample which comprises:

(a) preparing a solidified *Saccharomyces cerevisiae* culture using media containing agar and a β-galactosidase substrate selected from the group consisting of orthonitrophenyl-β-D-galactoside and 5-bromo-4-chloro-3-indoyl-β-D-galactoside and a strain of *S. cerevisiae* containing a hmg1⁻ mutation and a gene fusion of a structural gene for bacterial β-galactosidase with a yeast lanosterol 14-α-demethylase clone containing upstream promoter sequences as well as sequences for structural lanosterol 14-α-demethylase;

(b) adding said test sample to a disk or well in the culture;

(c) adding to another disk or well in the culture a positive control comprising a known lanosterol 14-α-demethylase inhibitor selected from the group consisting of ketoconazole, miconazole, econazole, dinaconazole, and itraconazole;

(d) incubating said test sample and said positive control in the culture for such time under such conditions sufficient to observe yeast cell growth in culture areas containing no test sample;

(e) assaying for β-galactosidase activity in the culture by observation of a halo of color around the positive control; and (f) determining the presence of ergosterol biosynthesis inhibition by the test sample by observation of a halo of color surrounding the test sample as compoted to the positive control.

18. A method according to claim 17 wherein the β-galactosidase substrate is 5-bromo-4-chloro-3-indoyl-β-D-galactoside and the positive control is dinaconazole.

\* \* \* \* \*